THIAZOLIDINE-SUBSTITUTED PHENYL SULFONAMIDES

FIELD OF THE INVENTION

This invention relates to certain 3-(thiazolidin-2'-yl)-4-hydroxy-phenyl sulfonamides useful as intermediates in the preparation of photographic image dye-providing materials.

BACKGROUND OF THE INVENTION

U.S. Pat. No. 3,719,489 describes and claims photographic processes employing initially photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Compounds disclosed as useful in liberating a reagent in the presence of said silver ions and/or silver complex are sulfur-nitrogen compounds containing the group

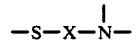

or —S—X—N= wherein X is

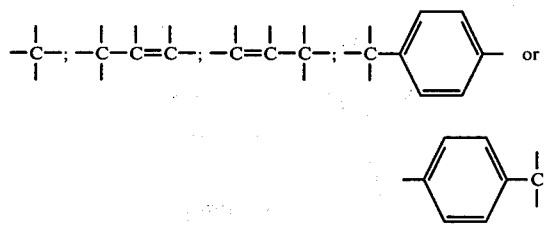 or 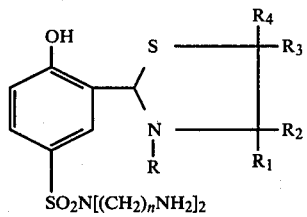

These 1,3-sulfur-nitrogen compounds may be linear or cyclic in structure, and in a preferred embodiment are cyclic compounds, such as, thiazolidine compounds which comprise a dye radical having the chromophoric system of an azo, anthraquinone, phthalocyanine or other dye and a thiazolidin-2'-yl moiety which may be bonded directly to the dye radical or through an appropriate linking group.

U.S. Pat. No. 4,098,783, a continuation-in-part of Ser. No. 465,694, now abandoned, which is a division of said U.S. Pat. No. 3,719,489 discloses that dyes substituted with a thiazolidin-2'-yl moiety may be synthesized by condensing a dye possessing an aldehyde group with a 2-aminoethanethiol, or rather than forming the thiazolidin-2-yl moiety as the final step in the synthesis, an intermediate possessing an aldehyde group may be condensed with the selected 2-aminoethanethiol and the condensation product then reacted with the appropriate molecule or molecules to yield the final dye product. For example, an intermediate comprising a linking group substituted with a thiazolidin-2'-yl moiety may be synthesized from a selected aldehyde in several steps including the condensation with a 2-aminoethanethiol and the linking group then reacted as an amine with a dye radical possessing, e.g., a sulfonyl chloride substituent or it may be reacted as a sulfonyl chloride with a dye radical possessing an amino substituent.

U.S. Pat. No. 4,355,169 of Donald A. McGowan and Frank A. Meneghini discloses and claims certain thiazolidine-substituted phenyl sulfonamides derived from alkylene diamines, namely, 3-(thiazolidin-2'-yl)-4-hydroxy-phenyl-w-aminoethylsulfonamides.

The present invention is directed to a different class of thiazolidine-substituted phenyl sulfonamides.

SUMMARY OF THE INVENTION

According to the present invention, a new class of 3-(thiazolidin-2'-yl)-4-hydroxy-phenyl sulfonamides is provided which are derived from bis(w-aminoalkyl)amines. Because they contain two free primary amino groups rather than one for reaction with the selected dye molecule, they may be used for synthesizing image dye-providing materials possessing one dye moiety together with an amino solubilizing group, of if desired, image dye-providing materials possessing two dye moieties.

It is, therefore, the pirmary object of the present invention to provide certain 3-(thiazolidin-2'-yl)-4-hydroxy-phenyl sulfonamides.

Other objects of the present invention will in part be obvious and will in part appear hereinafter.

The invention accordingly comprises the products and compositions possessing the features, properties and relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

Specifically, the 3-(thiazolidin-2'-yl)substituted phenyl sulfonamides of the present invention may be represented by the formula wherein R is selected from alkyl, aryl, aralkyl and alkaryl; $R_1$, $R_2$, $R_3$ and $R_4$ each are selected from hydrogen, alkyl, aryl, aralkyl and alkaryl; and m is 2 to 10.

United States Patent [19]

Herchen et al.

[11] 4,415,737

[45] Nov. 15, 1983

[54] THIAZOLIDINE-SUBSTITUTED PHENYL SULFONAMIDES

[75] Inventors: Stephen R. Herchen, Duxbury; David Messersmith, Cambridge, both of Mass.

[73] Assignee: Polaroid Corporation, Cambridge, Mass.

[21] Appl. No.: 451,349

[22] Filed: Dec. 20, 1982

[51] Int. Cl.³ .......................................... C07D 277/04
[52] U.S. Cl. ..................................................... 548/146
[58] Field of Search ........................................ 548/146

[56] References Cited

U.S. PATENT DOCUMENTS 4,355,169 10/1982 McGowan .......................... 548/146

Primary Examiner—Robert Gerstl
Attorney, Agent, or Firm—Sybil A. Campbell

[57] ABSTRACT

This invention is concerned with certain 3-(thiazolidin-2'-yl)-substituted phenyl sulfonamides which find utility as intermediates in the preparation of photographic image dye-providing materials.

5 Claims, No Drawings

As noted above, the sulfonamides of the subject invention are useful as intermediates in the synthesis of photographic image dye-providing materials, such as, the thiazolidine-substituted dyes described in aforementioned U.S. Pat. Nos. 3,719,489 and 4,098,783. For this purpose, the subject compounds may be reacted with a dye substituted with, e.g., a —COCl or —SO₂Cl group to give the image dye-providing material.

Examples of other image dye-providing compounds that may be prepared from the subject intermediates are those disclosed in U.S. Pat. No. 4,264,701.

Since certain changes may be made in the herein described subject matter without departing from the scope of the invention herein involved, it is intended that all matter contained in the above description and examples be interpreted as illustrative and not in a limiting sense.

What is claimed is:

1. A compound of the formula

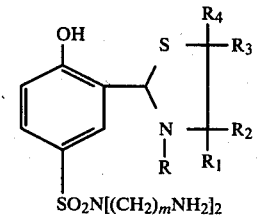

wherein R is selected from alkyl, aryl, aralkyl and alkaryl; $R_1$, $R_2$, $R_3$, $R_4$ each are selected from hydrogen, alkyl, aryl, aralkyl and alkaryl; and m is 2 to 10.

2. A compound as defined in claim 1 wherein R is alkyl.

3. A compound as defined in claim 1 wherein $R_3$ and $R_4$ are alkyl.

4. A compound as defined in claim 1 wherein n is 2.

5. The compound

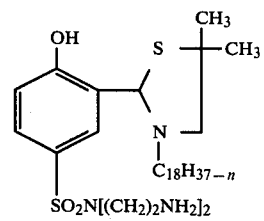

* * * * *